(12) United States Patent
Tashiro

(10) Patent No.: US 12,339,731 B2
(45) Date of Patent: Jun. 24, 2025

(54) ULTRASOUND SYSTEM AND CONTROL METHOD OF ULTRASOUND SYSTEM

(71) Applicant: FUJIFILM Corporation, Tokyo (JP)

(72) Inventor: Rika Tashiro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 187 days.

(21) Appl. No.: 18/151,187

(22) Filed: Jan. 6, 2023

(65) Prior Publication Data

US 2023/0153192 A1 May 18, 2023

Related U.S. Application Data

(63) Continuation of application No. PCT/JP2021/008940, filed on Mar. 8, 2021.

(30) Foreign Application Priority Data

Jul. 16, 2020 (JP) .................................. 2020-122102

(51) Int. Cl.
*G06F 11/00* (2006.01)
*A61B 8/00* (2006.01)
*G06F 11/07* (2006.01)

(52) U.S. Cl.
CPC ............ *G06F 11/0781* (2013.01); *A61B 8/58* (2013.01); *G06F 11/0736* (2013.01)

(58) Field of Classification Search
CPC .......................... G06F 11/0781; G06F 11/0736
(Continued)

(56) References Cited

U.S. PATENT DOCUMENTS

| 7,373,376 B1 * | 5/2008 | Hamer | H04L 67/535 |
| | | | 714/39 |
| 2002/0047862 A1 * | 4/2002 | Aoki | H04L 12/6418 |
| | | | 709/224 |

(Continued)

FOREIGN PATENT DOCUMENTS

| JP | 2001-084074 A | 3/2001 |
| JP | 2008-282086 A | 11/2008 |

(Continued)

OTHER PUBLICATIONS

The extended European search report issued by the European Patent Office on Sep. 8, 2023, which corresponds to European Patent Application No. 21841645.1-1126 and is related to U.S. Appl. No. 18/151,187.

(Continued)

*Primary Examiner* — Sarai E Butler
(74) *Attorney, Agent, or Firm* — Studebaker Brackett PLLC

(57) ABSTRACT

In an ultrasound system and a control method of the ultrasound system, in a case where occurrence of an error is detected, first operation information as at least one piece of operation information with the highest priority among a plurality of pieces of operation information corresponding to a type of the error that has occurred is displayed, and in a case where the number of times of the operation corresponding to the first operation information, which is performed by the user, has reached a predetermined number within a predetermined period after the first operation information is displayed, second operation information as at least one piece of operation information with the highest priority next to the first operation information is displayed.

20 Claims, 8 Drawing Sheets

(58) Field of Classification Search
USPC .................................................... 714/1–57
See application file for complete search history.

(56) References Cited

U.S. PATENT DOCUMENTS

| | | | | | |
|---|---|---|---|---|---|
| 2004/0078628 | A1* | 4/2004 | Akamatu | ............... | G06F 9/4881 |
| | | | | | 714/E11.132 |
| 2004/0078720 | A1* | 4/2004 | Ito | ................... | G06F 11/008 |
| | | | | | 714/45 |
| 2006/0224921 | A1* | 10/2006 | Marimuthu | ......... | G06F 11/3684 |
| | | | | | 714/25 |
| 2009/0106603 | A1* | 4/2009 | Dilman | ................ | G06F 11/327 |
| | | | | | 714/E11.002 |
| 2009/0327826 | A1* | 12/2009 | Inoue | ................... | H04L 1/0072 |
| | | | | | 714/748 |
| 2010/0146325 | A1* | 6/2010 | John | ................... | G06F 11/0748 |
| | | | | | 714/E11.023 |
| 2011/0105904 | A1 | 5/2011 | Watanabe | | |
| 2011/0154136 | A1* | 6/2011 | Osuki | ................... | H04L 67/02 |
| | | | | | 709/204 |
| 2012/0226161 | A1* | 9/2012 | Pelissier | ............... | A61B 8/467 |
| | | | | | 600/443 |
| 2013/0226001 | A1 | 8/2013 | Steen et al. | | |
| 2016/0170686 | A1* | 6/2016 | Haas | ................... | G06F 3/121 |
| | | | | | 358/1.14 |
| 2016/0321347 | A1* | 11/2016 | Zhou | ................... | G06Q 30/06 |
| 2017/0053486 | A1* | 2/2017 | Takeda | ............... | G07F 17/3234 |
| 2017/0192698 | A1* | 7/2017 | Cilfone | ................ | G06F 3/0652 |
| 2018/0368812 | A1 | 12/2018 | Kim et al. | | |
| 2019/0324833 | A1* | 10/2019 | Kobayashi | ........... | G06F 3/1234 |
| 2020/0138408 | A1* | 5/2020 | Zheng | ................. | A61B 8/4472 |
| 2021/0409518 | A1* | 12/2021 | Logan | ................... | H04L 67/01 |

FOREIGN PATENT DOCUMENTS

| | | |
|---|---|---|
| JP | 2009-116787 A | 5/2009 |
| JP | 2013-172959 A | 9/2013 |
| JP | 2017-169666 A | 9/2017 |
| JP | 2019-115480 A | 7/2019 |
| WO | 2010/122791 A1 | 10/2010 |

OTHER PUBLICATIONS

Sobhani M. Rahim et al., "Portable low cost ultrasound imaging system", 2016 IEEE International Ultrasonics Symposium (IUS), Sep. 18, 2016, pp. 1-4, doi: 10.1109/ULTSYM.2016.7728837, IEEE.
International Search Report issued in PCT/JP2021/008940; mailed Apr. 6, 2021.
International Preliminary Report On Patentability (Chapter I) and Written Opinion of the International Searching Authority issued in PCT/JP2021/008940; issued Jan. 17, 2023.

* cited by examiner

ULTRASOUND SYSTEM AND CONTROL METHOD OF ULTRASOUND SYSTEM

CROSS-REFERENCE TO RELATED APPLICATIONS

This application is a Continuation of PCT International Application No. PCT/JP2021/008940 filed on Mar. 8, 2021, which claims priority under 35 U.S.C. § 119(a) to Japanese Patent Application No. 2020-122102 filed on Jul. 16, 2020. The above applications are hereby expressly incorporated by reference, in its entirety, into the present application.

BACKGROUND OF THE INVENTION

1. Field of the Invention

The present invention relates to an ultrasound system in which an ultrasound probe and a handheld information terminal are connected in a wired or wireless manner, and a control method of the ultrasound system.

2. Description of the Related Art

In the related art, in the medical field, an ultrasound system using an ultrasound image has been put to practical use. In general, an ultrasound system comprises an ultrasound probe with a built-in transducer array, and an information terminal connected to the ultrasound probe, and the ultrasound system causes the ultrasound probe to transmit an ultrasound beam toward a subject, receives an ultrasound echo from the subject by the ultrasound probe, and electrically processes a reception signal thereof to generate an ultrasound image.

In recent years, portable and handheld ultrasound systems have been developed, as well as stationary ultrasound systems. The portable ultrasound system is an ultrasound-dedicated system in which an information terminal is realized by a laptop terminal device. On the other hand, in the handheld ultrasound system, an information terminal is realized by a handheld terminal device such as a smartphone or a tablet personal computer (PC), and an ultrasound diagnosis application program running on the terminal device.

Here, there are JP2009-116787A, JP2008-282086A, JP2001-084074A, and JP2013-172959A as the documents in the related art that are references for the present invention.

JP2009-116787A relates to an information providing device and the like. JP2009-116787A discloses that a repeated operation by a user is detected, an operation history of the detected repeated operation is analyzed, an operation history stored in a storage unit such as an internal storage unit and an external storage unit is referred to from operation information that is stored corresponding to the operation history in the storage unit, the operation information corresponding to the operation history of the analyzed repeated operation is specified, and the specified operation information is output.

JP2008-282086A relates to an incorrect operation prevention device and the like. JP2008-282086A discloses that an operation that is performed on an operation screen by an operator is stored, the operation for which an error display was made on the operation screen among the stored operations are counted, and in a case where a count value exceeds a predetermined value set in advance, control is performed such that a specific operation of which the count value exceeds the predetermined value cannot be performed on the operation screen or a message that the specific operation is incorrect.

JP2001-084074A relates to an incorrect operation prevention device of a medical apparatus. JP2001-084074A discloses that in the medical apparatus that has a soft key for executing desired processing by an operation of touching or clicking an operation button displayed on a screen of a display device, execution of the desired processing is started by continuing to operate the operation button for a predetermined time or by repeating the operation for a predetermined number of times within a predetermined time.

JP2013-172959A relates to a portable ultrasound imaging system and the like. JP2013-172959A discloses that, in the ultrasound imaging system including an ultrasound probe and a portable host system configured to receive information from the ultrasound probe, the host system displays the ultrasound probe specified by the host system, and an operator touches a corresponding icon to select one of the displayed probes.

SUMMARY OF THE INVENTION

Since the handheld ultrasound system has a smaller display screen as compared with the stationary and portable ultrasound systems, the information amount that can be notified to a user at once by displaying a message is limited. Therefore, in a case where an error has occurred, only the main information for resolving the error can be displayed at once, so that the user cannot resolve the error even by performing an operation corresponding to the main information, and thus the same operation is repeated, which is the problem.

For example, it is assumed that a wireless connection error has occurred in a case where the user wirelessly connects the ultrasound probe and the information terminal. In order to solve the wireless connection error, originally, there may be various kinds of information described in a user guide or the like, but due to the small display screen of the handheld ultrasound system, only the main information among the various kinds of information can be displayed at once. Therefore, the user cannot resolve the connection error even by performing an operation corresponding to the main information, and thus the same operation is repeated.

Thus, an object of the present invention is to provide an ultrasound system and a control method of the ultrasound system, which resolve the problem in the related art and can support a user to resolve an error without repeating the same operation.

In order to achieve the object, an aspect of the present invention provides an ultrasound system comprising an ultrasound probe; and a handheld information terminal connected to the ultrasound probe in a wired or wireless manner, in which the information terminal includes an operation information storage unit that stores a plurality of pieces of operation information corresponding to an operation, which is performed by a user for resolving an error, for each type of the error, and an error processing unit that, in a case where occurrence of the error is detected, displays first operation information as at least one piece of operation information with the highest priority among the plurality of pieces of operation information corresponding to the type of the error that has occurred, and in a case where the number of times of the operation corresponding to the first operation information, which is performed by the user, has reached a predetermined number within a predetermined period after the first operation information is displayed, displays second operation information as at least one piece of operation information with the highest priority next to the first operation information.

Here, it is preferable that, in a case where n and m are integers equal to or greater than 1, the maximum value of n is m, and the number of times of the operation corresponding to n-th operation information, which is performed by the user, has reached the predetermined number within the predetermined period after the n-th operation information is displayed, the error processing unit performs displaying (n+1)-th operation information as at least one piece of operation information with the highest priority next to the n-th operation information, once or more by increasing n from 1 to m by one.

It is preferable that, in a case where the number of times of the operation corresponding to (m+1)-th operation information, which is performed by the user, has reached the predetermined number within the predetermined period after the (m+1)-th operation information is displayed, the error processing unit displays reference destination information representing a reference destination of related information that relates to the error.

It is preferable that the error processing unit displays the reference destination information in a link format or a code format.

It is preferable that the related information is a user guide of the ultrasound system stored in the information terminal or a server connected to the information terminal via a network.

It is preferable that the related information is a web page containing information relating to the error, which is stored in a server connected to the information terminal via a network.

It is preferable that the web page includes at least one of a question and answer web page and an inquiry form web page.

It is preferable that the reference destination information is information on a reference destination of a program installed in the information terminal, and in a case where the information on the reference destination of the program is selected by the user, the program is activated.

It is preferable that the error processing unit sequentially displays each operation information from the first operation information to (m+1)-th operation information on each of a plurality of pages in a page format in which the plurality of pages are sequentially displayed.

Another aspect of the present invention provides an ultrasound system comprising an ultrasound probe; a handheld information terminal connected to the ultrasound probe in a wired or wireless manner; and a server connected to the information terminal via a network, in which the information terminal includes an operation information storage unit that stores a plurality of pieces of operation information corresponding to an operation, which is performed by a user for resolving an error, for each type of the error, and an error processing unit that, in a case where occurrence of the error is detected, displays first operation information as at least one piece of operation information with the highest priority among the plurality of pieces of operation information corresponding to the type of the error that has occurred, and in a case where the number of times of the operation corresponding to the first operation information, which is performed by the user, has reached a predetermined number within a predetermined period after the first operation information is displayed, displays server-side operation information corresponding to information on the type of the error that has occurred and information on the number of times of the operation, which is received from the server.

It is preferable that the error processing unit is configured as a program for causing a computer to function as the error processing unit, and in a case where the number of times of the operation has reached the predetermined number within the predetermined period, displays server-side operation information corresponding to information on the type of the error that has occurred, information on the number of times of the operation, and information on a version of the program, which is received from the server.

Another aspect of the present invention provides an ultrasound system comprising an ultrasound probe; and a handheld information terminal connected to the ultrasound probe in a wired or wireless manner, in which the information terminal includes an operation information storage unit that stores a plurality of pieces of operation information corresponding to an operation, which is performed by a user for resolving an error, for each type of the error, and an error processing unit that, in a case where occurrence of the error is detected, displays first operation information as at least one piece of operation information with the highest priority among the plurality of pieces of operation information corresponding to the type of the error that has occurred, and in a case where the number of times of the operation corresponding to the first operation information, which is performed by the user, has reached a predetermined number within a predetermined period after the first operation information is displayed, reads second operation information as at least one piece of operation information with the highest priority next to the first operation information, by sound.

Another aspect of the present invention provides an ultrasound system comprising an ultrasound probe; and a handheld information terminal connected to the ultrasound probe in a wired or wireless manner, in which the information terminal includes an operation information storage unit that stores a plurality of pieces of operation information corresponding to an operation, which is performed by a user for resolving an error, for each type of the error, and an error processing unit that, in a case where occurrence of the error is detected, displays first operation information as at least one piece of operation information with the highest priority among the plurality of pieces of operation information corresponding to the type of the error that has occurred, and in a case where the number of times of the operation corresponding to the first operation information, which is performed by the user, has reached a predetermined number within a predetermined period after the first operation information is displayed, displays reference destination information representing a reference destination of related information that relates to the error.

Another aspect of the present invention provides a control method of an ultrasound system including an ultrasound probe, and a handheld information terminal connected to the ultrasound probe in a wired or wireless manner, and the control method comprises storing a plurality of pieces of operation information corresponding to an operation, which is performed by a user for resolving an error, for each type of the error, by an operation information storage unit of the information terminal; displaying, in a case where occurrence of the error is detected, first operation information as at least one piece of operation information with the highest priority among the plurality of pieces of operation information corresponding to the type of the error that has occurred, by an error processing unit of the information terminal; and displaying, in a case where the number of times of the operation corresponding to the first operation information, which is performed by the user, has reached a predetermined number within a predetermined period after the first operation information is displayed, second operation information as at least one piece of operation information with the highest priority next to the first operation information, by the error processing unit.

In the present invention, in a case where the occurrence of the error is detected, the first operation information and the second operation information with the highest priority among the plurality of pieces of operation information corresponding to the type of the error that has occurred are sequentially displayed, and therefore, the user can perform an operation corresponding to the second operation information after performing an operation corresponding to the first operation information the predetermined number of times within the predetermined period. Therefore, according to the present invention, it is possible to support the user to resolve the error without repeating the same operation.

DESCRIPTION OF THE PREFERRED EMBODIMENTS

Hereinafter, an ultrasound system and a control method of the ultrasound system according to the present invention will be described in detail on the basis of preferred embodiments illustrated in the accompanying drawings.

Figure 1:
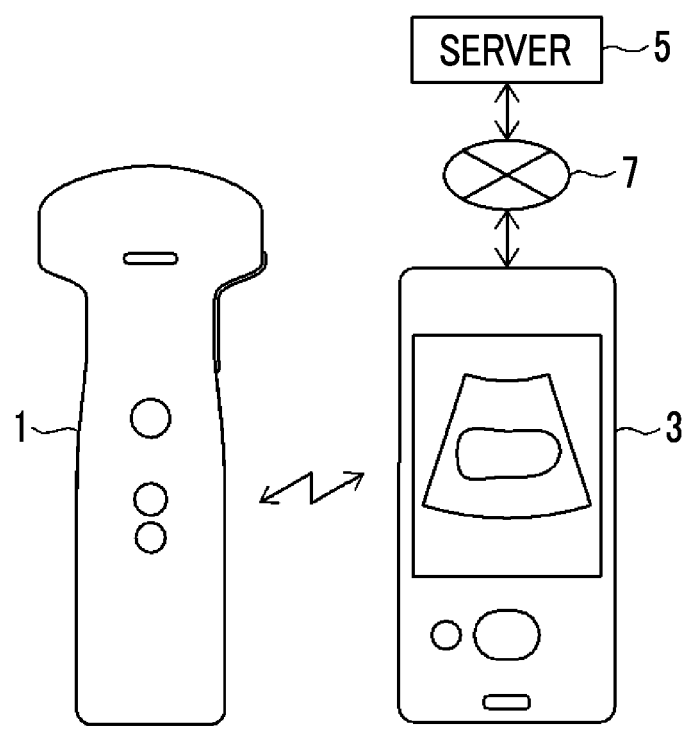
FIG. 1 is a block diagram illustrating a configuration of an ultrasound system of an embodiment according to the present invention.

FIG. 1 is a block diagram illustrating a configuration of an ultrasound system of an embodiment according to the present invention. The ultrasound system illustrated in FIG. 1 comprises an ultrasound probe 1, a handheld information terminal 3 connected to the ultrasound probe 1 in a wired or wireless manner, and a server 5. The ultrasound system of the present embodiment is realized by the ultrasound probe 1, the handheld information terminal 3, and an ultrasound diagnosis application program running on the information terminal 3.

Figure 2:
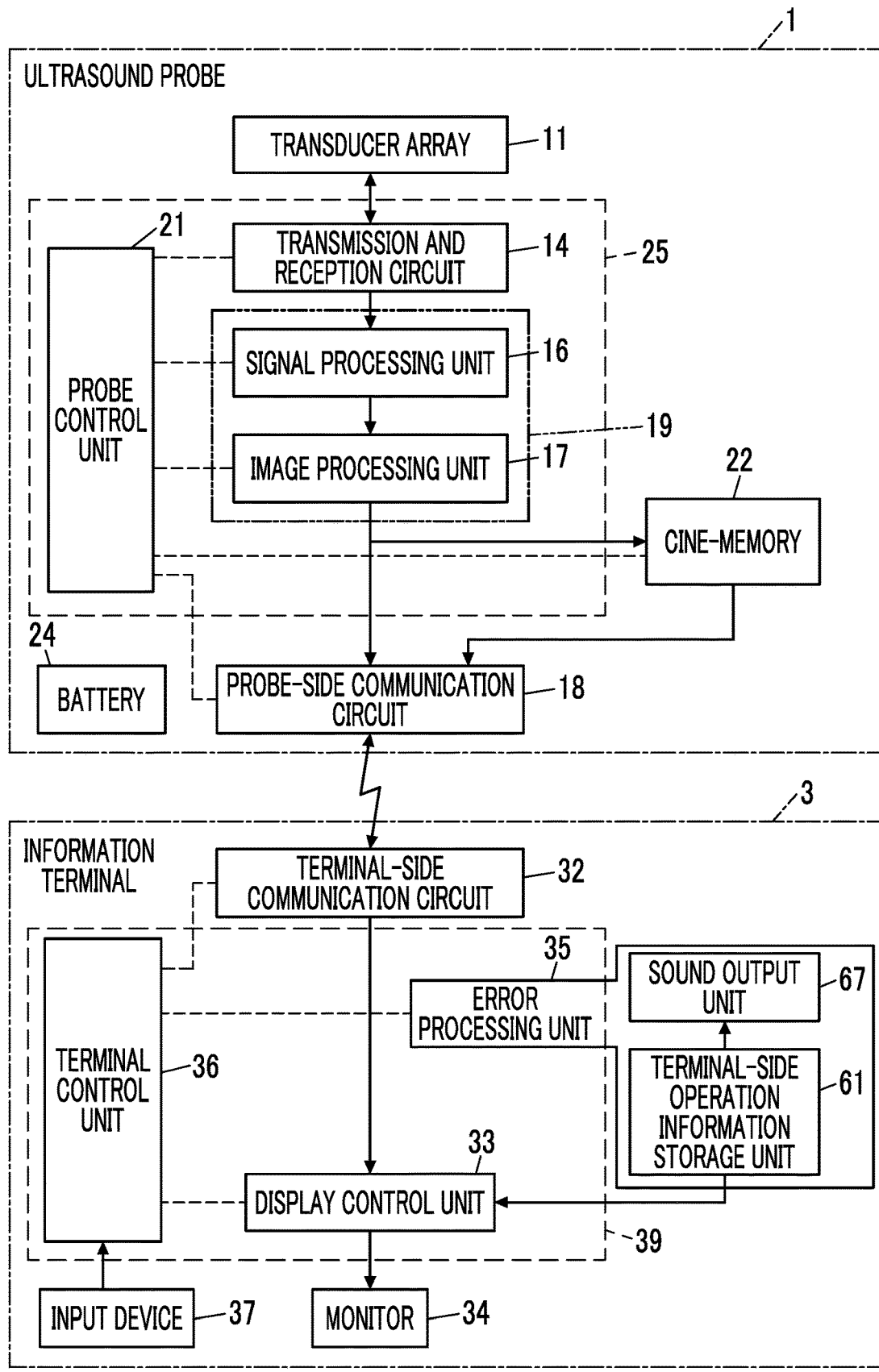
FIG. 2 is a block diagram illustrating configurations of an ultrasound probe and an information terminal.

The ultrasound probe 1 captures an ultrasound image by scanning a subject using ultrasound beams, and outputs data corresponding to the ultrasound image, that is, image information data of the ultrasound image in the case of the present embodiment. As illustrated in FIG. 2, the ultrasound probe 1 comprises a transducer array 11, a transmission and reception circuit 14, a signal processing unit 16, an image processing unit 17, a probe-side communication circuit 18, a probe control unit 21, a cine-memory 22, and a battery 24.

The transmission and reception circuit 14 is bidirectionally connected to the transducer array 11. The signal processing unit 16, the image processing unit 17, and the probe-side communication circuit 18 are sequentially connected in series to the transmission and reception circuit 14. The signal processing unit 16 and the image processing unit 17 constitute an image information data generation unit 19. Further, the cine-memory 22 is connected to the image processing unit 17, and the probe-side communication circuit 18 is connected to the cine-memory 22.

Further, the probe control unit 21 is connected to the transmission and reception circuit 14, the signal processing unit 16, the image processing unit 17, the cine-memory 22, and the probe-side communication circuit 18. The battery 24 is built in the ultrasound probe 1.

The transmission and reception circuit 14, the image information data generation unit 19 (the signal processing unit 16 and the image processing unit 17), and the probe control unit 21 constitute a probe-side processor 25.

The transducer array 11 has a plurality of ultrasonic transducers arranged in a one-dimensional or two-dimensional manner. According to a drive signal supplied from the transmission and reception circuit 14, each of the transducers transmits an ultrasonic wave and receives a reflected wave from the subject to output an analog reception signal.

For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 3:
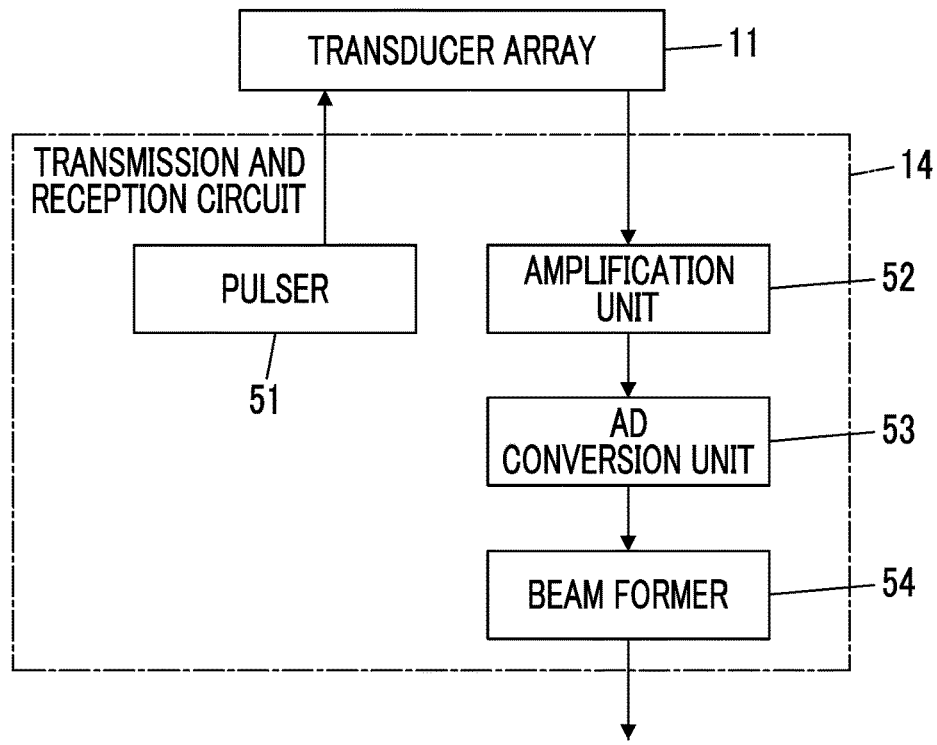
FIG. 3 is a block diagram illustrating a configuration of a transmission and reception circuit.

The transmission and reception circuit 14 causes the transducer array 11 to transmit the ultrasonic wave, and performs reception focusing processing on the reception signal output from the transducer array 11 that has received the ultrasound echo to generate a sound ray signal, under the control of the probe control unit 21. As illustrated in FIG. 3, the transmission and reception circuit 14 has a pulser 51 connected to the transducer array 11, and an amplification unit 52, an analog digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of transducers of the transducer array 11 form an ultrasound beam on the basis of a transmission delay pattern selected by the probe control unit 21, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 52.

The amplification unit 52 amplifies the signals input from each transducer constituting the transducer array 11, and transmits the amplified signals to the AD conversion unit 53. The AD conversion unit 53 converts the signal transmitted from the amplification unit 52 into digital reception data, and outputs the reception data to the beam former 54.

The beam former 54 performs so-called reception focusing processing in which addition is performed by giving delays to respective pieces of the reception data converted by the AD conversion unit 53 according to a sound speed distribution or a sound speed set on the basis of a reception delay pattern selected by the probe control unit 21. Through the reception focusing processing, a sound ray signal in which each piece of the reception data converted by the AD conversion unit 53 is phased and added and the focus of the ultrasound echo is narrowed is generated.

The image information data generation unit 19 generates image information data on the basis of the sound ray signal generated by the transmission and reception circuit 14. The image information data generation unit 19 has the signal processing unit 16 and the image processing unit 17 as described above.

The signal processing unit 16 generates image signal data before imaging into the ultrasound image, on the basis of the sound ray signal generated by the transmission and reception circuit 14, under the control of the probe control unit 21. More specifically, the signal processing unit 16 generates, as the image signal data before imaging, a signal representing tomographic image information regarding tissues inside the subject, by performing envelope detection processing after signal processing, for example, correcting the attenuation of the sound ray signal generated by the beam former 54 of the transmission and reception circuit 14, which is caused by the propagation distance according to the depth of the reflection position of the ultrasonic wave.

The image processing unit 17 generates the ultrasound image as the image information data generated by the image information data generation unit 19 on the basis of the image signal data generated by the signal processing unit 16, under the control of the probe control unit 21. More specifically, the image processing unit 17 raster-converts the image signal data before imaging, which is generated by the signal processing unit 16 into the image signal according to a normal television signal scanning method, performs various kinds of image processing such as brightness correction, gradation correction, sharpness correction, image size correction, refresh rate correction, scanning frequency correction, and color correction according to a display format of a monitor 34, on the image signal converted in this manner to generate the ultrasound image (ultrasound image signal), and then outputs the generated ultrasound image as the image information data to the probe-side communication circuit 18.

The cine-memory 22 stores the image information data generated by the image information data generation unit 19, under the control of the probe control unit 21. More specifically, the cine-memory 22 stores the ultrasound image generated by the image processing unit 17 of the image information data generation unit 19, as the image information data in the case of the live mode. The cine-memory 22 has a memory capacity for storing ultrasound images of several tens to several hundreds of frames in a case where ultrasound images for several seconds to several tens of seconds, for example, ultrasound images of 30 frames for one second are captured.

The cine-memory 22 is a ring buffer. Thus, in a case where the ultrasound images of past frames for the number of frames corresponding to the memory capacity are stored in the cine-memory 22, instead of the ultrasound image of the oldest frame, the ultrasound image of the latest frame is sequentially stored in the cine-memory 22. In this manner, the ultrasound images of the past frames for the number of frames corresponding to the memory capacity, from the ultrasound image of the latest frame are always stored in the cine-memory 22.

Here, the live mode is a mode in which the ultrasound images (video) captured at a certain frame rate are sequentially displayed (real time display).

A freeze mode is a mode in which the ultrasound images (video) captured in the case of the live mode are stored in the cine-memory 22 and the ultrasound images (static image) of any frames are read out and displayed from the ultrasound images (video) of the past frames stored in the cine-memory 22.

The probe-side communication circuit 18 transmits the image information data generated by the image processing unit 17 or the image information data stored in the cine-memory 22 in a wired or wireless manner under the control of the probe control unit 21.

In the present embodiment, the probe-side communication circuit 18 includes an antenna for transmitting and receiving radio waves, modulates a carrier on the basis of the ultrasound image generated by the image processing unit 17 to generate a transmission signal, and transmits radio waves from the antenna by supplying the transmission signal to the antenna to perform wireless transmission of the ultrasound image.

As the modulation method of the carrier, amplitude shift keying (ASK), phase shift keying (PSK), quadrature phase shift keying (QPSK), 16 quadrature amplitude modulation (16QAM), or the like is used.

Further, the probe-side communication circuit 18 can also connect the ultrasound probe 1 and the information terminal 3 in a wired manner using a cable such as a Universal Serial Bus (USB) cable.

The probe-side communication circuit 18 wirelessly transmits the image information data of the frame generated by the image information data generation unit 19 in the case of the live mode, and wirelessly transmits the image information data stored in the cine-memory 22 in the case of the freeze mode.

The probe control unit 21 controls each unit of the ultrasound probe 1 on the basis of a program and the like stored in advance. More specifically, the probe control unit 21 controls the transmission and reception circuit 14 such that transmission of ultrasound beams and reception of ultrasound echoes are performed on the basis of an examination mode and a scanning method set in advance. The probe control unit 21 controls the signal processing unit 16 and the image processing unit 17 of the image information data generation unit 19 such that signal processing set in advance is performed on the sound ray signal and the image processing set in advance is performed on the image signal data. The probe control unit 21 performs control such that the image information data generated by the image information data generation unit 19 is stored in the cine-memory 22 in the case of the live mode, and the ultrasound image of the past frame stored in the cine-memory 22 is read out in the case of the freeze mode. Further, the probe control unit 21 controls the probe-side communication circuit 18 such that the image signal data is transmitted with a transmission radio field intensity set in advance.

Here, the examination mode indicates any of examination modes that can be used in the ultrasound system, such as a brightness (B) mode, a color Doppler (CF) mode, a power Doppler (PD) mode, a motion (M) mode, a pulse wave Doppler (PW) mode, and a continuous wave Doppler (CW) mode, and the scanning method indicates any one of scanning methods such as an electronic sector scanning method, an electronic linear scanning method, and an electronic convex scanning method.

The battery 24 is built in the ultrasound probe 1, and supplies power to each circuit of the ultrasound probe 1.

Next, the information terminal 3 is a handheld terminal device such as a smartphone and a tablet PC, and displays the ultrasound image on the basis of data corresponding to the ultrasound image captured by the ultrasound probe 1. As illustrated in FIG. 2, the information terminal 3 comprises a terminal-side communication circuit 32, a display control unit 33, an error processing unit 35, a terminal control unit 36, a monitor (display unit) 34, and an input device 37.

The display control unit 33 and the monitor 34 are sequentially connected in series to the terminal-side communication circuit 32. Further, the terminal control unit 36 is connected to the terminal-side communication circuit 32, the display control unit 33, and the error processing unit 35. The input device 37 is connected to the terminal control unit 36.

In the present embodiment, the probe-side communication circuit 18 of the ultrasound probe 1 and the terminal-side communication circuit 32 of the information terminal 3 are connected in a wireless manner by wireless communication, and the ultrasound probe 1 and the information terminal 3 are connected so that the information can be bidirectionally delivered.

The terminal-side communication circuit 32 receives the image information data transmitted from the probe-side communication circuit 18 of the ultrasound probe 1 in a wired or wireless manner, under the control of the terminal control unit 36. In the present embodiment, the terminal-side communication circuit 32 includes an antenna for transmitting and receiving radio waves, receives a transmission signal wirelessly transmitted from the probe-side communication circuit 18 via the antenna, demodulates the received transmission signal, and outputs the ultrasound image (ultrasound image signal) as the image information data.

The display control unit 33 displays various kinds of information on the monitor 34 under the control of the terminal control unit 36. The display control unit 33 displays the ultrasound image on the monitor 34 on the basis of the image information data received by the terminal-side communication circuit 32, for example. More specifically, the display control unit 33 performs predetermined processing on the ultrasound image as the image information data to display the processed ultrasound image on the monitor 34. Further, in a case where an error has occurred in the ultrasound system, the display control unit 33 displays information on the type of the error that has occurred, and operation information or the like for resolving the error on the monitor 34.

Figure 4:
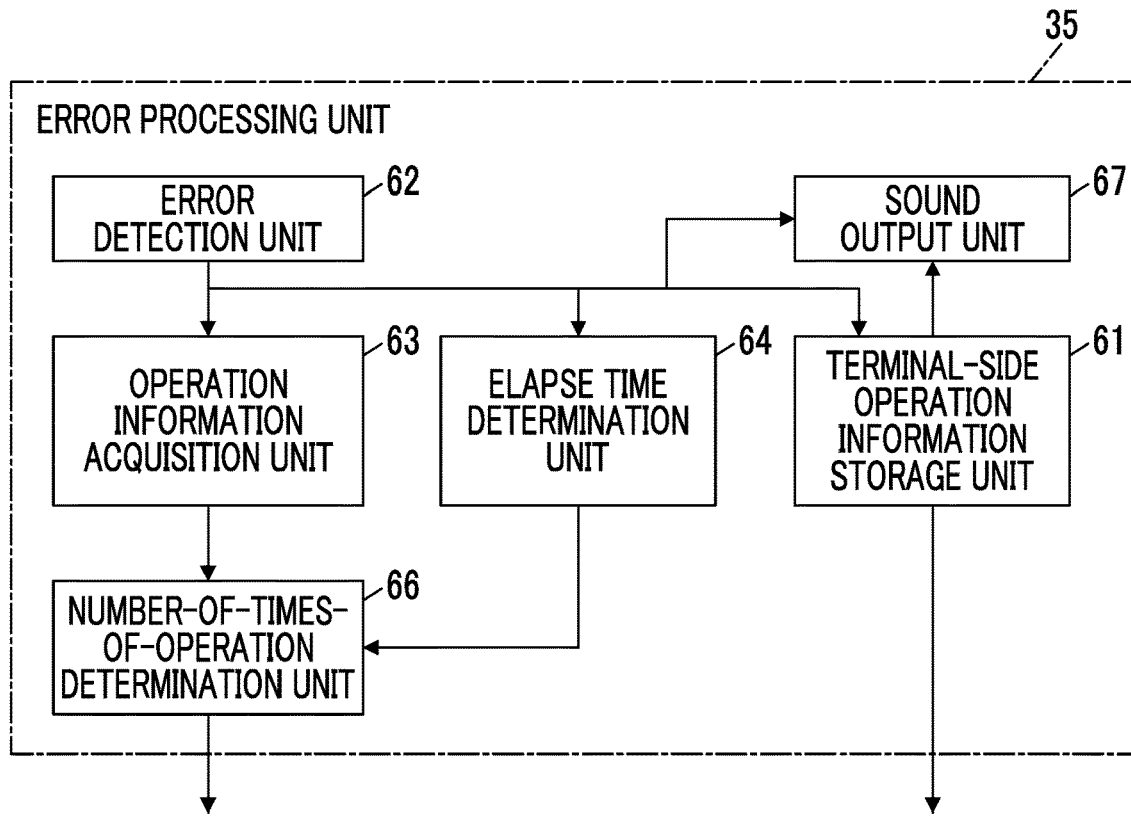
FIG. 4 is a block diagram illustrating a configuration of an error processing unit.

In a case where the occurrence of the error is detected in the ultrasound system, the error processing unit 35 displays the information on the type of the error that has occurred, and proposes the operation information or the like for resolving the error to a user (operator of the ultrasound system), under the control of the terminal control unit 36. As illustrated in FIG. 4, the error processing unit 35 comprises a terminal-side operation information storage unit 61, an error detection unit 62, an operation information acquisition unit 63, an elapse time determination unit 64, a number-of-times-of-operation determination unit 66, and a sound output unit 67.

The type of the error is not particularly limited, but includes, for example, an error at the time of wireless connection or connection using a wired cable between the ultrasound probe 1 and the information terminal 3, an error at the time of inputting patient information of a patient for which the ultrasound image is to be captured, and an error such as an operation mistake and a setting mistake by the user in addition to the failure of the ultrasound system.

The operation information is various kinds of information (advice) to be proposed to the user in order to resolve an error that has occurred in a case where the error has occurred, and includes information on an operation procedure or the like that the user performs for resolving the error. The operation information may be a text message, a video, sound, or the like, and is not particularly limited. However, for example, the operation information for resolving the wireless connection error includes information on an operation of tapping a scan button of the ultrasound diagnosis application program, an operation of tapping a probe addition button, an operation of tapping a probe switch button, and the like.

The operation information acquisition unit 63 and the number-of-times-of-operation determination unit 66 are sequentially connected in series to the error detection unit 62. Further, the elapse time determination unit 64 is connected to the error detection unit 62, and the number-of-times-of-operation determination unit 66 is connected to the elapse time determination unit 64. The sound output unit 67 is connected to the terminal-side operation information storage unit 61 and the error detection unit 62. The terminal-side operation information storage unit 61 is connected to the error detection unit 62, and the display control unit 33 is connected to the terminal-side operation information storage unit 61 and the number-of-times-of-operation determination unit 66.

The terminal-side operation information storage unit 61 stores a plurality of pieces of operation information corresponding to the operation performed by the user for resolving the error, for each type of the error occurring in the ultrasound system. The terminal-side operation information storage unit 61 stores a plurality of pieces of operation information corresponding to the operation performed by the user for resolving the wireless connection error, for example.

The error detection unit 62 detects whether or not an error has occurred in the ultrasound system. The error detection unit 62 detects whether or not a wireless connection error including an error such as an operation mistake and a setting mistake has occurred.

A method of detecting the occurrence of an error is not particularly limited, but includes, for example, checking whether or not the setting of the wireless connection between the ultrasound probe 1 and the information terminal 3 is correct, detecting whether or not the ultrasound probe 1 and the information terminal 3 are connected in a wired manner, detecting whether or not the input of the patient information is correct, and the like.

In a case where the occurrence of the error is detected by the error detection unit 62, the operation information acquisition unit 63 acquires the user operation information that is information on the operation performed by the user who reads the operation information for resolving the error that has occurred.

The operation of the user is not particularly limited, but includes, for example, an operation of performing the setting of the wireless connection between the ultrasound probe 1 and the information terminal 3, an operation of connecting the ultrasound probe 1 and the information terminal 3 using a wired cable, an operation of re-inputting the correct patient information, and the like.

The elapse time determination unit 64 determines whether or not an elapse time from the detection of the occurrence of the error has passed a predetermined period.

The elapse time determination unit 64 measures the elapse time using a timer or the like, and determines whether the measured elapse time has passed the predetermined period, for example, two minutes.

In a case where the elapse time determination unit 64 determines that the elapse time has not elapsed the predetermined period, the number-of-times-of-operation determination unit 66 determines whether or not the number of times of the operation corresponding to the operation information, which is performed by the user, has reached a predetermined number within the predetermined period on the basis of the user operation information acquired by the operation information acquisition unit 63.

For example, the number-of-times-of-operation determination unit 66 counts the number of times the setting of the wireless connection of the information terminal 3 is performed by the user within the predetermined period from the detection of the occurrence of the error, using a counter or the like, and determines whether or not the count value has reached the predetermined number, for example, two.

The sound output unit 67 reads out various kinds of information by sound, and includes, for example, a speaker, earphones, headphones, and the like.

The terminal control unit 36 controls each unit of the information terminal 3 on the basis of a program stored in advance and an instruction or the like of the user input from the input device 37. More specifically, the terminal control unit 36 controls the terminal-side communication circuit 32 such that the reception of the transmission signal from the probe-side communication circuit 18 of the ultrasound probe 1 is performed. Further, the terminal control unit 36 controls the display control unit 33 such that the ultrasound image is displayed on the monitor 34 on the basis of the image information data. In a case where an error has occurred, the terminal control unit 36 controls the error processing unit 35 to propose the operation information for resolving the error that has occurred, to the user.

The display control unit 33, the error detection unit 62, the operation information acquisition unit 63, the elapse time determination unit 64, and the number-of-times-of-operation determination unit 66 of the error processing unit 35, and the terminal control unit 36 constitute a terminal-side processor 39.

The monitor 34 displays various kinds of information. The monitor 34 displays, for example, the information on the type of the error, the operation information, and the ultrasound image generated by the display control unit 33.

Examples of the monitor 34 include a display device such as a liquid crystal display (LCD), and an organic electroluminescence (EL) display.

The input device 37 is for the user to perform an input operation to input various instructions, and includes a touch panel and the like by which the user can perform a touch operation to input various instructions, in the present embodiment.

Figure 5:
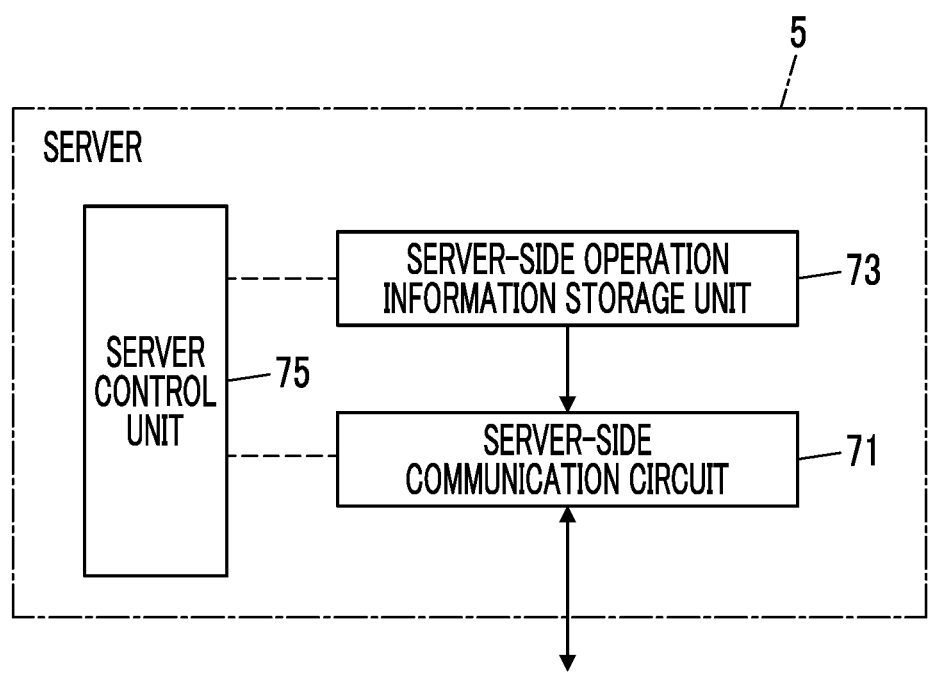
FIG. 5 is a block diagram illustrating a configuration of a server.

In a case where an error has occurred, the server 5 provides the server-side operation information corresponding to the request from the information terminal 3, to the information terminal 3. As illustrated in FIG. 5, the server 5 comprises a server-side communication circuit 71, a server-side operation information storage unit 73, and a server control unit 75.

The server-side communication circuit 71 is connected to the server-side operation information storage unit 73. The server control unit 75 is connected to the server-side communication circuit 71 and the server-side operation information storage unit 73.

As illustrated in FIG. 1, the server-side communication circuit 71 of the server 5 and the terminal-side communication circuit 32 of the information terminal 3 are connected via a communication line (network) 7 such as wireless fidelity (Wi-Fi), the Internet, and a telephone line, and thus the server 5 and the information terminal 3 are connected such that the information can be bidirectionally delivered.

The server-side communication circuit 71 receives various kinds of information transmitted from the terminal-side communication circuit 32 of the information terminal 3, and transmits the operation information read out from the server-side operation information storage unit 73 to the information terminal 3 under the control of the server control unit 75.

Similarly to the terminal-side operation information storage unit 61 of the information terminal 3, the server-side operation information storage unit 73 stores a plurality of pieces of server-side operation information for resolving the error, for each type of the error.

The server-side operation information is not particularly limited, and may be the same as or different from the operation information stored in the terminal-side operation information storage unit 61, for example.

The server control unit 75 controls each unit of the server 5 on the basis of a program and the like stored in advance. More specifically, the server control unit 75 controls the server-side communication circuit 71 such that the reception of data from the terminal-side communication circuit 32 is performed. Further, the server control unit 75 reads out the server-side operation information corresponding to the request from the information terminal 3, from the server-side operation information storage unit 73, and controls the server-side communication circuit 71 such that the server-side operation information read out from the server-side operation information storage unit 73 is transmitted to the terminal-side communication circuit 32.

Note that the ultrasound system does not necessarily include the server 5.

Figure 6:
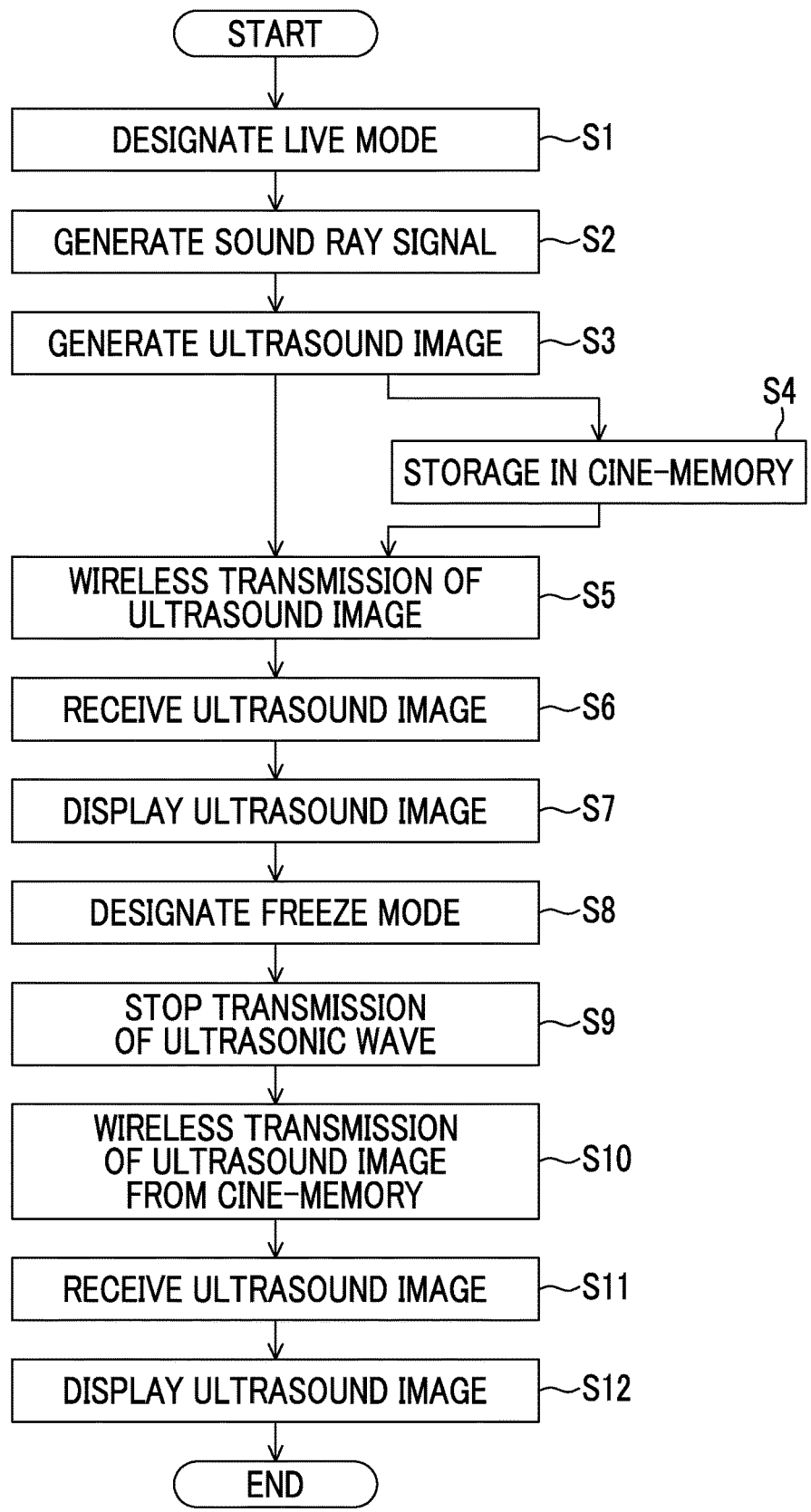
FIG. 6 is a flowchart illustrating an operation of the ultrasound system.

Next, the operation of the ultrasound system will be described with reference to the flowchart of FIG. 6. First, the operation of the ultrasound system in the case of the live mode will be described.

In a case where the live mode is designated on the basis of the user's instruction input from the input device 37 (Step S1), in a state where the ultrasound probe 1 is in contact with the body surface of the subject, the transmission of the ultrasonic waves is started by the transmission and reception circuit 14, and the sound ray signal is generated (Step S2).

That is, under the control of the probe control unit 21, ultrasound beams are transmitted into the subject from the plurality of transducers of the transducer array 11 according to the drive signal from the pulser 51 of the transmission and reception circuit 14.

Ultrasound echoes from the subject based on the ultrasound beams transmitted from the pulser 51 are received by each transducer of the transducer array 11, and the reception signal as an analog signal is output from each transducer of the transducer array 11, which has received the ultrasound echo.

The reception signal as the analog signal output from each transducer of the transducer array 11 is amplified by the amplification unit 52 of the transmission and reception circuit 14, and is subjected to AD conversion by the AD conversion unit 53, and thereby the reception data is acquired.

By performing the reception focusing processing on the reception data by the beam former 54, the sound ray signal is generated.

Next, the ultrasound image is generated as the image information data by the image information data generation unit 19 on the basis of the sound ray signal generated by the beam former 54 of the transmission and reception circuit 14 (Step S3).

That is, the sound ray signal generated by the beam former 54 is subjected to various kinds of signal processing by the signal processing unit 16 of the image information data generation unit 19, and the signal representing tomographic image information regarding tissues inside the subject is generated as the image signal data before imaging.

The image signal data generated by the signal processing unit 16 is raster-converted by the image processing unit 17, and is further subjected to various kinds of image processing, and the ultrasound image is generated as the image information data.

The ultrasound image generated by the image processing unit 17 is stored in the cine-memory 22 (Step S4).

Further, the ultrasound image generated by the image processing unit 17 is wirelessly transmitted from the probe-side communication circuit 18 to the information terminal 3 (Step S5).

Next, the ultrasound image wirelessly transmitted from the probe-side communication circuit 18 of the ultrasound probe 1 is received by the terminal-side communication circuit 32 under the control of the terminal control unit 36 of the information terminal 3 (Step S6).

Next, the display control unit 33 performs predetermined processing on the ultrasound image received by the terminal-side communication circuit 32 to display the processed ultrasound image on the monitor 34 (Step S7).

That is, in the case of the live mode, as the image information data, the ultrasound image generated by the image processing unit 17 of the image information data generation unit 19 of the ultrasound probe 1 is wirelessly transmitted from the probe-side communication circuit 18. On the other hand, the display control unit 33 of the information terminal 3 displays the ultrasound image received by the terminal-side communication circuit 32 on the monitor 34.

Next, the operation of the ultrasound system in the case of the freeze mode will be described.

In a case where the freeze mode is designated on the basis of the user's instruction input from the input device 37 (Step S8), the transmission of the ultrasonic waves from the transducer array 11 is stopped (Step S9).

In this case, as the image information data, the ultrasound images of the past frames stored in the cine-memory 22 are read out and wirelessly transmitted from the probe-side communication circuit 18 (Step S10).

Next, the ultrasound image wirelessly transmitted from the probe-side communication circuit 18 is received by the terminal-side communication circuit 32 (Step S11).

Next, the display control unit 33 displays the ultrasound image of the past frame received by the terminal-side communication circuit 32 on the monitor 34 (Step S12).

Next, the operation of the ultrasound system in a case where the ultrasound probe 1 and the information terminal 3 are wirelessly connected will be described with reference to the flowchart of FIG. 7.

First, the user wirelessly connects the ultrasound probe 1 and the information terminal 3 (Step S21). In this case, for example, the user selects the ultrasound probe 1 to be used, from the list of a plurality of registered ultrasound probes by tapping the ultrasound probe 1.

In a case where the ultrasound probe 1 to be used is selected, whether or not a wireless connection error has occurred between the ultrasound probe 1 and the information terminal 3 is detected by the error detection unit 62 (Step S22).

As a result, in a case where the occurrence of the error is not detected (NO in Step S22), the wireless connection between the ultrasound probe 1 and the information terminal 3 is established (Step S23). In this manner, the ultrasound image corresponding to the image information data, which is transmitted from the ultrasound probe 1 and is received by the information terminal 3, is displayed on the monitor 34.

On the other hand, in a case where the occurrence of the error is detected (YES in Step S22), an elapse time T is set to T=0 (initialized) by the elapse time determination unit 64, and the number of times of the operation N is set to N=0 (initialized) by the number-of-times-of-operation determination unit 66 (Step S24).

Figure 8:
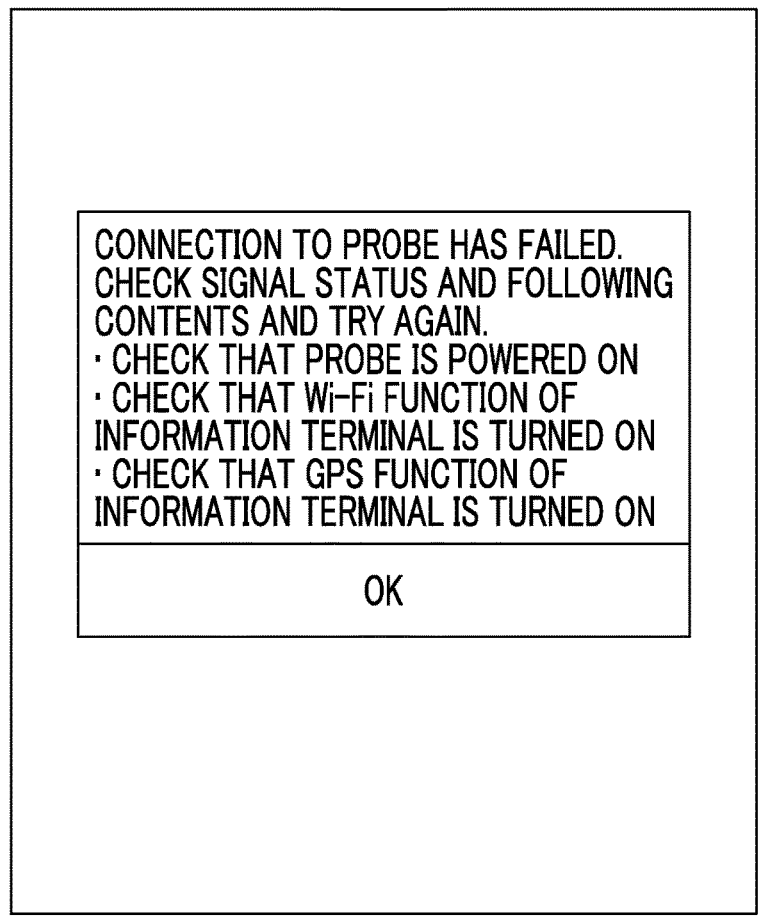
FIG. 8 is a conceptual diagram of a display screen of a monitor illustrating information on a type of an error and first operation information.

A plurality of pieces of operation information corresponding to the wireless connection error are read out from the terminal-side operation information storage unit 61, and the first operation information that is at least one piece of the operation information is selected from the pieces of operation information with a high priority among the plurality of pieces of read operation information. Then, as illustrated in FIG. 8, the information on the type of the error that has occurred and the first operation information are displayed on the monitor 34 by the display control unit 33 (Step S25).

The user reads the information on the type of the error displayed on the monitor 34, understands that a wireless connection error has occurred between the ultrasound probe 1 and the information terminal 3, similarly reads the first operation information, and performs an operation corresponding to the first operation information for resolving the error (Step S26). In a case where an operation corresponding to the first operation information is performed by the user, the user operation information is acquired by the operation information acquisition unit 63.

In a case where it is found that the operation corresponding to the first operation information is performed by the user on the basis of the user operation information, the number of times of the operation N is set to N=N+1 by the number-of-times-of-operation determination unit 66 (Step S27).

Whether or not a wireless connection error has occurred between the ultrasound probe 1 and the information terminal 3, that is, whether or not the error is resolved by the user's operation is detected by the error detection unit 62 (Step S28).

As a result, in a case where the occurrence of the error is not detected (NO in Step S28), that is, in a case where the error is resolved by the user's operation, the processing proceeds to Step S23, and the ultrasound image is displayed on the monitor 34.

On the other hand, in a case where it is detected that an error has occurred (YES in Step S28), that is, in a case where the error is not resolved by the user's operation, subsequently, whether or not the elapse time T from the detection of the occurrence of the error has passed a predetermined period T1, for example, two minutes (T≥T1?) is determined by the elapse time determination unit 64 (Step S29).

As a result, in a case where the elapse time T has passed the predetermined period T1 (YES in Step S29), the processing returns to Step S21, and starts again from the beginning. It means that, in a case where the elapse time T has passed the predetermined period T1, the same operation is not repeatedly performed by the user in a short time, in other words, the user starts again the wireless connection from the beginning so that the same operation is performed, for example, after one hour or the next day from the detection of the occurrence of the error.

On the other hand, in a case where the elapse time T has not passed the predetermined period T1 (NO in Step S29), whether or not the number of times of the operation N has reached a predetermined number N1, for example, two (N≥N1?) is determined by the number-of-times-of-operation determination unit 66 (Step S30).

As a result, in a case where the number of times of the operation N has not reached the predetermined number N1 (NO in Step S30), the processing proceeds to Step S26. Thus, the user performs again the operation corresponding to the first operation information, for example. That is, the user repeats the same operation.

On the other hand, in a case where the number of times of the operation N has reached the predetermined number N1 (YES in Step S30), second operation information that is at least one piece of the operation information with the highest priority next to the first operation information among the plurality of pieces of operation information corresponding to the wireless connection error is displayed on the monitor 34 by the display control unit 33 (Step S31).

Subsequently, the user reads the second operation information displayed on the monitor 34, and performs an operation corresponding to the second operation information (Step S32).

As described above, in the ultrasound system, in a case where the occurrence of the error is detected, the display control unit 33 displays the first operation information among the plurality of pieces of operation information corresponding to the type of the error that has occurred, on the monitor 34.

In the following order, the user operation information of the operation corresponding to the first operation information, which is performed by the user who reads the first operation information, is acquired by the operation information acquisition unit 63, whether or not the elapse time from the detection of the occurrence of the error has passed the predetermined period is determined by the elapse time determination unit 64, and in a case where it is determined that the elapse time has not passed the predetermined period, whether or not the number of times of the operation corresponding to the first operation information, which is performed by the user within the predetermined period, has reached the predetermined number is determined by the number-of-times-of-operation determination unit 66 on the basis of the user operation information.

Then, in a case where the number of times of the operation has reached the predetermined number within the predetermined period after the first operation information is displayed, the display control unit 33 displays the second operation information on the monitor 34.

In this manner, in the ultrasound system, in a case where the occurrence of the error is detected, the first operation information and the second operation information with the highest priority among the plurality of pieces of operation information corresponding to the type of the error that has occurred are sequentially displayed, and therefore, the user can perform an operation corresponding to the second operation information after performing an operation corresponding to the first operation information the predetermined number of times within the predetermined period. Therefore, with the ultrasound system, it is possible to support the user to resolve the error without repeating the same operation.

Note that the number of pieces of the operation information displayed at once can be set according to the screen size of the monitor 34. For example, in a case where the screen size of the monitor 34 is small, one piece of the operation information is displayed at once, and in a case where the screen size is large, three pieces of the operation information are displayed at once. Further, the number of pieces of the operation information displayed at once may be set to the same number or different numbers in each stage of displaying the operation information.

The wireless connection error has been described as an example, but the present invention is not limited thereto, and can be similarly applied to various errors occurring in the ultrasound system.

For example, it is assumed that in a case where patient information is input and is tried to be "registered", information on an error of "invalid characters are used" is displayed.

In this case, for example, the following operation information of (A1) to (A4) is displayed in order.

(A1) "Please check that the patient name does not contain inappropriate symbols (@, <, >, . . . , and the like)"
(A2) "Please check that the patient ID does not contain inappropriate symbols (@, <, >, . . . , and the like)"
(A3) "Please check that the date is correct"
(A4) "Please check that the date and time setting of the information terminal is correct"

It is assumed that the ultrasound probe 1 and the information terminal 3 are connected using a wired cable, but the information on the error and the operation information (first operation information) such as "Disconnected from the probe due to the failure of probe setting. Please check the signal status and reconnect with the probe" are displayed.

In this case, for example, the following operation information of (B1) to (B4) is displayed in order.

(B1) "Please disconnect and connect the wired cable and wait a few seconds"
(B2) "Please turn off the power of the probe, turn it on again, and wait a few seconds"
(B3) "Please disconnect and connect the wired cable again and wait a few seconds"
(B4) "Please 'end' the application once, disconnect and connect the wired cable, wait a few seconds, and then reactivate the application"

Further, sequentially displaying the operation information in two stages has been described as an example, but the present invention is not limited thereto, and the operation information may be sequentially displayed in three or more stages.

In this case, in the ultrasound system, n and m are integers equal to or greater than 1, the maximum value of n is m, and the display control unit 33 displays n-th operation information among the plurality of pieces of operation information corresponding to the type of the error that has occurred, on the monitor 34.

In the following order, the user operation information of the operation corresponding to the n-th operation information, which is performed by the user who reads the n-th operation information, is acquired by the operation information acquisition unit 63, whether or not the elapse time from the detection of the occurrence of the error has passed the predetermined period is determined by the elapse time determination unit 64, and in a case where it is determined that the elapse time has not passed the predetermined period, whether or not the number of times of the operation corresponding to the n-th operation information, which is performed by the user within the predetermined period, has reached the predetermined number is determined by the number-of-times-of-operation determination unit 66 on the basis of the user operation information.

Then, in a case where the number of times of the operation has reached the predetermined number within the predetermined period after the display control unit displays the n-th operation information, displaying (n+1)-th operation information that is at least one piece of the operation information with the highest priority next to the n-th operation information is performed once or more by increasing n from 1 to m by one.

Figure 9:
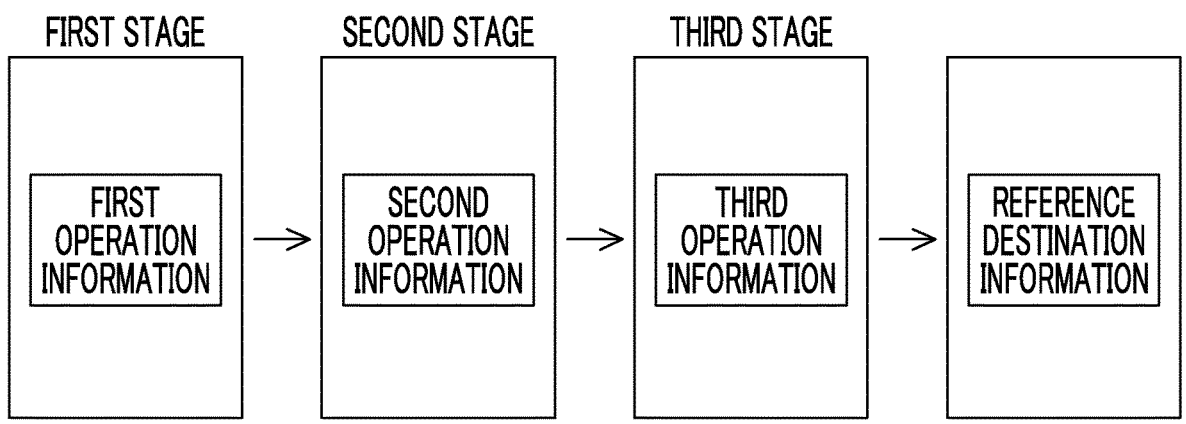
FIG. 9 is a conceptual diagram of a display screen of a monitor in a case where reference destination information is displayed after the operation information is displayed in three stages.

For example, in a case where m=2, that is, in a case where a plurality of pieces of operation information are displayed in three stages, as illustrated in FIG. 9, in a case where, with n=1, the first operation information in the first stage is displayed and then the number of times of the operation corresponding to the first operation information has reached the predetermined number within the predetermined period, the second operation information in the second stage is displayed. In a case where, with n=2, the second operation information in the second stage is displayed and then the number of times of the operation corresponding to the second operation information has reached the predetermined number within the predetermined period, third operation information in the third stage is displayed.

In a case where the number of times of the operation corresponding to (m+1)-th operation information, which is performed by the user, has reached the predetermined number within the predetermined period after the (m+1)-th operation information is displayed, the display control unit 33 may display reference destination information representing a reference destination of related information relating to the error. In this case, in a case where the reference destination information is tapped to be selected by the user, the related information corresponding to the reference destination information is displayed.

For example, in a case where a plurality of pieces of operation information are displayed in three stages of the first operation information, the second operation information, and the third operation information, as illustrated in FIG. 9, in a case where the number of times of the operation corresponding to the third operation information has reached the predetermined number within the predetermined period after the third operation information in the third (last) stage is displayed, the display control unit 33 displays the reference destination information, and in a case where the reference destination information is tapped to be selected by the user, the display control unit 33 displays the related information corresponding to the reference destination information.

The related information is information of more general content, which relates to the error, such as information on the ultrasound system and information on Wi-Fi, but less relates to the error than the operation information.

The related information is not particularly limited, but may be a user guide of the ultrasound system stored in the information terminal 3 or may be the user guide of the ultrasound system stored in the server 5. For example, the display control unit 33 displays a page of the user guide, which corresponds to the error that has occurred.

Further, the related information may also be a web page containing information relating to the error stored in the server 5. The web page can include at least one of a Question and Answer (Q&A) web page and an inquiry form web page.

Even in a case where the error cannot be resolved by the operation corresponding to the operation information, there is a possibility that the user can resolve the error by referring to the related information.

The reference destination information is information representing the location where the related information is stored, such as the reference destination of the related information, for example, a folder in the information terminal and a web address of the server.

The display control unit 33 can display the reference destination information in a link format or a code format represented by a multi-dimensional code of two or more dimensions such as a quick response (QR) code.

For example, the related information corresponding to the reference destination information, which is selected by the user tapping the reference destination information in a link format displayed on the monitor 34 or by reading a QR code (registered trademark) using the information terminal 3 itself or another information terminal, is displayed.

The reference destination information may be various programs installed in the information terminal 3. Examples of various programs include a program that supports the resolution of the error and a program that detects the state of a communication environment using an automatic answering system by sound.

For example, in a case where the reference destination information is selected by the user tapping an icon of the program displayed on the monitor 34 as the reference destination information, the program corresponding to the tapped icon is activated.

Even in a case where the error cannot be resolved by the operation corresponding to the operation information, there is a possibility that the user can resolve the error by using various programs.

Further, the display control unit 33 may sequentially display each operation information from the first operation information to the (m+1)-th operation information on each of a plurality of pages in a page format in which the plurality of pages are sequentially displayed.

For example, in a case where the first operation information, the second operation information, and the third operation information are sequentially displayed, the display control unit 33 respectively displays the first operation information, the second operation information, and the third operation information on the first page, the second page, and the third page in a page format.

By displaying the operation information in a page format, the user can sequentially refer to the operation information of each page by swiping and turning the pages. That is, the user can refer to all of the plurality of pieces of operation information corresponding to the type of the error.

The display of the operation information, the related information, and the reference destination information in a case where a wireless connection error has occurred between the ultrasound probe 1 and the information terminal 3 has been described as an example.

Example of the operation information in a case where a wireless connection error has occurred are illustrated in the following (1) to (12). In the operation information of (1) to (12), the operation information of (1) has the highest priority, the priority becomes lower in order of (1) to (12), and the operation information of (12) has the lowest priority. The priority of the operation information of (1) to (12) is increased in descending order of the possibility that the error can be resolved in a case where the user performs an operation corresponding to the operation information of (1) to (12).

(1) Check that the ultrasound probe is powered on.
(2) Check that the Wi-Fi function of the information terminal is turned on.
(3) Check that the Global Positioning System (GPS) function (positional information) of the information terminal is turned on.
(4) Connect the ultrasound probe and the information terminal in a wireless manner.
(5) End the ultrasound diagnosis application program, and then reactivate the ultrasound diagnosis application program.
(6) Turn off the power of ultrasound probe to be connected, and then turn on the power of the ultrasound probe again.
(7) Delete the ultrasound probe to be connected from the list of the registered ultrasound probes.
(8) Delete all saved networks from the list of the saved networks.
(9) Register the ultrasound probe to be connected again.
(10) Perform an operation corresponding to the operation information of (4) again.
(11) Change the location and connect the ultrasound probe and the information terminal in a wireless manner.
(12) Connect the ultrasound probe and the information terminal in a wired manner.

In this case, in a case where the occurrence of the wireless connection error is detected, the display control unit 33 displays three pieces of operation information (first operation information) of (1) to (3) with the highest priority from among the operation information of (1) to (12) corresponding to the wireless connection error, on the monitor 34.

In a case where the number of times of the operation corresponding to the operation information of (1) to (3), which is performed by the user, has reached the predetermined number within the predetermined period, the display control unit 33 displays three pieces of operation information (second operation information) of (4) to (6) with the next highest priority. In a case where the number of times of the operation corresponding to the operation information of (4) to (6) has reached the predetermined number within the predetermined period, the display control unit 33 displays three pieces of operation information (third operation information) of (7) to (9) with the next highest priority. In a case where the number of times of the operation corresponding to the operation information of (7) to (9) has reached the predetermined number within the predetermined period, the display control unit 33 displays three pieces of operation information (fourth operation information) of (10) to (12) with the next highest priority.

In a case where the number of times of the operation corresponding to the operation information of (10) to (12) has reached the predetermined number within the predetermined period after the final operation information of (10) to (12) is displayed, the display control unit 33 displays the related information or the reference destination information.

The display control unit 33 may display the server-side operation information instead of displaying the second operation information.

In this case, in a case where the occurrence of the error is detected, the display control unit 33 displays the first operation information among the plurality of pieces of operation information corresponding to the type of the error that has occurred, on the monitor 34.

Next, in a case where the number of times of the operation has reached the predetermined number within the predetermined period after the first operation information is displayed, the probe-side communication circuit 18 transmits, for example, the information on the type of the error that has occurred and the information on the number of times of the operation to the server 5, and receives the server-side operation information corresponding to the information on the type of the error that has occurred and the information on the number of times of the operation from the server 5.

Then, the display control unit 33 displays the server-side operation information corresponding to the information on the type of the error that has occurred and the information on the number of times of the operation, which is received from the server 5, on the monitor 34.

Figure 10:
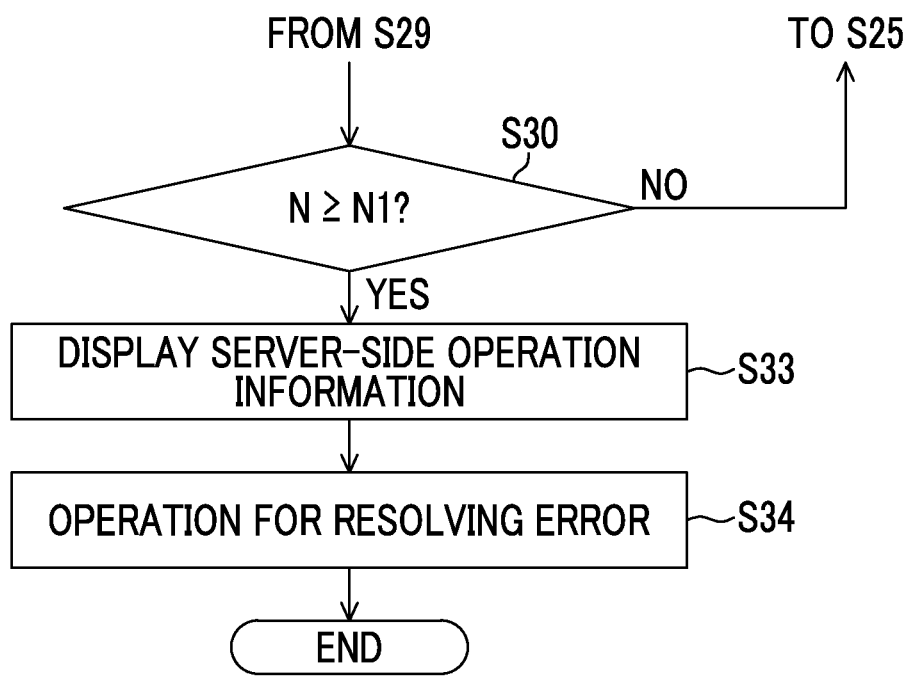
FIG. 10 is a flowchart illustrating an operation of the ultrasound system in a case where server-side operation information is displayed.

The operation of the ultrasound system in a case where the server-side operation information is displayed will be described with reference to the flowchart of FIG. 10.

Figure 7:
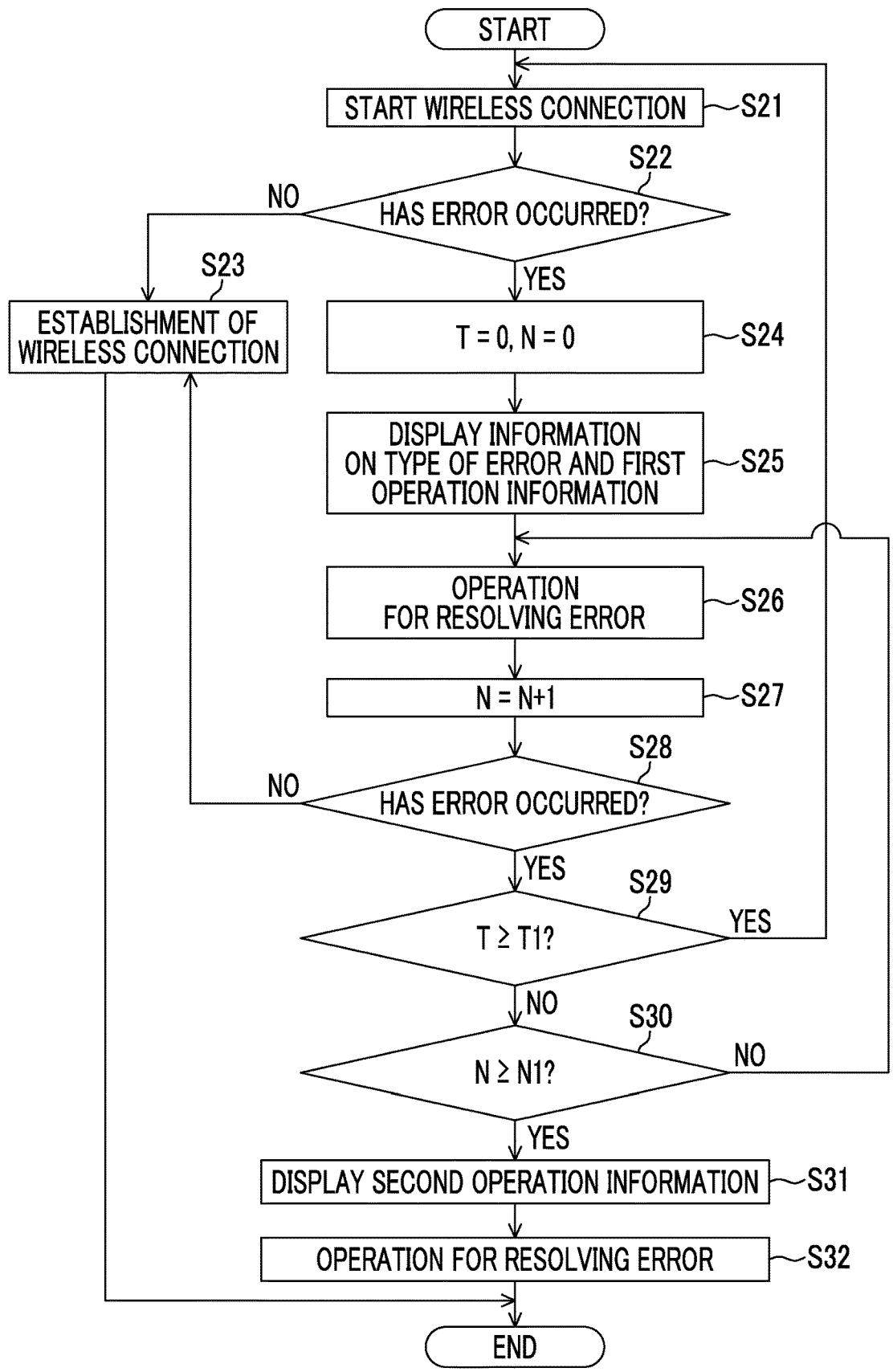
FIG. 7 is a flowchart illustrating an operation of the ultrasound system in a case where the ultrasound probe and the information terminal are wirelessly connected.

The operation until, as a result of determination from Step S21 to Step S30, the number of times of the operation N has not reached the predetermined number N1 (NO in Step S30), is the same as that in the flowchart of FIG. 7, and thus repeated description will be omitted.

In a case where, as a result of the determination of Step S30, the number of times of the operation N has reached the predetermined number N1 (YES in Step S30), for example, the information on the type of the error that has occurred and the information on the number of times of the operation are transmitted to the server 5 by the probe-side communication circuit 18, and the server-side operation information corresponding to the information on the type of the error that has occurred and the information on the number of times of the operation are receives from the server 5 by the probe-side communication circuit 18.

Then, the server-side operation information corresponding to the information on the type of the error that has occurred and the information on the number of times of the operation, which is received from the server 5, is displayed on the monitor 34 by the display control unit 33 (Step S33).

Subsequently, the user reads the server-side operation information displayed on the monitor 34, and performs an operation corresponding to the server-side operation information (Step S34).

The latest server-side operation information is always stored in the server-side operation information storage unit 73 of the server 5. In other words, the latest server-side operation information can always be provided to the user by updating the server-side operation information stored in the server-side operation information storage unit 73. In this manner, the user can refer to the latest server-side operation information corresponding to the information on the type of the error that has occurred and the information on the number of times of the operation.

The display control unit 33, the error detection unit 62, the operation information acquisition unit 63, the elapse time determination unit 64, the number-of-times-of-operation determination unit 66, and the terminal control unit 36 can be configured as a program for causing the terminal-side processor 39 (computer) to function as the display control unit 33, the error detection unit 62, the operation information acquisition unit 63, the elapse time determination unit 64, the number-of-times-of-operation determination unit 66, and the terminal control unit 36.

In this case, the probe-side communication circuit 18 may transmit the information on the type of the error that has occurred, the information on the number of times of the operation, and the information on the version of the program to the server 5, receive the server-side operation information corresponding to the information on the type of the error that has occurred, the information on the number of times of the operation, and the information on the version of the program from the server 5, and display the server-side operation information corresponding to the information on the type of the error that has occurred, the information on the number of times of the operation, and the information on the version of the program, which is received from the server 5, on the monitor 34.

In this manner, the display control unit 33 can display the latest server-side operation information corresponding to the information on the type of the error that has occurred and the information on the number of times of the operation, for each version of the program.

Instead of displaying the second operation information by the display control unit 33 or before the second operation information is displayed by the display control unit 33, the sound output unit 67 may read the second operation information by sound.

In this case, in a case where the occurrence of the error is detected, the display control unit displays the first operation information among the plurality of pieces of operation information corresponding to the type of the error that has occurred, on the monitor 34.

Then, in a case where the number of times of the operation has reached the predetermined number within the predetermined period after the first operation information is displayed, the sound output unit 67 reads the second operation information by sound.

In this manner, the user can listen to the second operation information by sound while reading the first operation information displayed on the monitor 34. Further, by reading the second operation information by sound, the content of the second operation information can be proposed to the user regardless of the size of the display screen of the information terminal 3.

The display control unit 33 may display the reference destination information instead of displaying the second operation information.

In this case, in a case where the occurrence of the error is detected, the display control unit 33 displays the first operation information among the plurality of pieces of operation information corresponding to the type of the error that has occurred, on the monitor 34.

Next, in a case where the number of times of the operation has reached the predetermined number within the predetermined period after the first operation information is displayed, the display control unit 33 displays the reference destination information.

In this manner, after the first operation information is displayed, the reference destination information may be displayed instead of displaying the second operation information.

The image processing unit 17 may be provided to the information terminal 3 instead of being provided to the ultrasound probe 1. In this case, image signal data before imaging into the ultrasound image is generated by the signal processing unit 16, the image signal data generated by the signal processing unit 16 is wirelessly transmitted from the probe-side communication circuit 18 of the ultrasound probe 1 to the terminal-side communication circuit 32 of the information terminal 3, and the ultrasound image is generated on the basis of the image signal data by the image processing unit of the information terminal 3.

In this case, in the information terminal 3, since the ultrasound image is generated by performing the image processing on the image signal data, there is an advantage that image processing conditions such as gain can be freely changed according to the display characteristics of the monitor 34 after the ultrasound image is displayed on the monitor 34.

In the device of the present invention, the hardware configurations of the processing units executing various kinds of processing such as the transmission and reception circuit 14, the signal processing unit 16, the image processing unit 17, the probe control unit 21, the display control unit 33, the error detection unit 62, the operation information acquisition unit 63, the elapse time determination unit 64, the number-of-times-of-operation determination unit 66, the terminal control unit 36, the server control unit 75, and the like may be dedicated hardware, or may be various processors or computers that execute programs. The hardware configuration of the cine-memory 22, the terminal-side operation information storage unit 61, the server-side operation information storage unit 73, and the like may be dedicated hardware, or may be a memory such as a semiconductor memory and a storage device such as a hard disk drive (HDD) and a solid state drive (SSD).

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing a specific process such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor fulfilling the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: information terminal
5: server
7: communication line
11: transducer array
14: transmission and reception circuit
16: signal processing unit
17: image processing unit
18: probe-side communication circuit
19: image information data generation unit
21: probe control unit
22: cine-memory
24: battery
25: probe-side processor
32: terminal-side communication circuit
33: display control unit
34: monitor
35: error processing unit
36: terminal control unit
37: input device
39: terminal-side processor
51: pulser
52: amplification unit
53: AD conversion unit
54: beam former
61: terminal-side operation information storage unit
62: error detection unit
63: operation information acquisition unit
64: elapse time determination unit
66: number-of-times-of-operation determination unit
67: sound output unit
71: server-side communication circuit
73: server-side operation information storage unit
75: server control unit

What is claimed is:

1. An ultrasound system comprising:
an ultrasound probe; and
a handheld information terminal connected to the ultrasound probe in a wired or wireless manner,
wherein the information terminal includes
an operation information storage unit that stores a plurality of pieces of operation information corresponding to an operation, which is performed by a user for resolving an error, for each type of the error, and
an error processing unit that, in a case where occurrence of the error is detected, displays first operation information as at least one piece of operation information with a highest priority among the plurality of pieces of operation information corresponding to the type of the error that has occurred, and in a case where a number of times of the operation corresponding to the first operation information, which is performed by the user, has reached a predetermined number within a predetermined period after the first operation information is displayed, displays second operation information as at least one piece of operation information with the highest priority next to the first operation information.

2. The ultrasound system according to claim 1,
wherein in a case where n and m are integers equal to or greater than 1, a maximum value of n is m, and the number of times of the operation corresponding to n-th operation information, which is performed by the user, has reached the predetermined number within the predetermined period after the n-th operation information is displayed, the error processing unit performs displaying (n+1)-th operation information as at least one piece of operation information with the highest priority next to the n-th operation information, once or more by increasing n from 1 to m by one.

3. The ultrasound system according to claim 2,
wherein the error processing unit sequentially displays each operation information from the first operation information to (m+1)-th operation information on each of a plurality of pages in a page format in which the plurality of pages are sequentially displayed.

4. The ultrasound system according to claim 2,
wherein in a case where the number of times of the operation corresponding to (m+1)-th operation information, which is performed by the user, has reached the predetermined number within the predetermined period after the (m+1)-th operation information is displayed, the error processing unit displays reference destination information representing a reference destination of related information that relates to the error.

5. The ultrasound system according to claim 4,
wherein the error processing unit sequentially displays each operation information from the first operation information to (m+1)-th operation information on each of a plurality of pages in a page format in which the plurality of pages are sequentially displayed.

6. The ultrasound system according to claim 4,
wherein the error processing unit displays the reference destination information in a link format or a code format.

7. The ultrasound system according to claim 6,
wherein the related information is a user guide of the ultrasound system stored in the information terminal or a server connected to the information terminal via a network.

8. The ultrasound system according to claim 6,
wherein the related information is a web page containing information relating to the error, which is stored in a server connected to the information terminal via a network.

9. The ultrasound system according to claim 8,
wherein the web page includes at least one of a question and answer web page and an inquiry form web page.

10. The ultrasound system according to claim 6,
wherein the reference destination information is information on a reference destination of a program installed in the information terminal, and in a case where the information on the reference destination of the program is selected by the user, the program is activated.

11. The ultrasound system according to claim 4,
wherein the related information is a user guide of the ultrasound system stored in the information terminal or a server connected to the information terminal via a network.

12. The ultrasound system according to claim 11,
wherein the reference destination information is information on a reference destination of a program installed in the information terminal, and in a case where the information on the reference destination of the program is selected by the user, the program is activated.

13. The ultrasound system according to claim 4,
wherein the related information is a web page containing information relating to the error, which is stored in a server connected to the information terminal via a network.

14. The ultrasound system according to claim 13,
wherein the web page includes at least one of a question and answer web page and an inquiry form web page.

15. The ultrasound system according to claim 4,
wherein the reference destination information is information on a reference destination of a program installed in the information terminal, and in a case where the information on the reference destination of the program is selected by the user, the program is activated.

16. An ultrasound system comprising:
an ultrasound probe;
a handheld information terminal connected to the ultrasound probe in a wired or wireless manner; and
a server connected to the information terminal via a network,
wherein the information terminal includes
an operation information storage unit that stores a plurality of pieces of operation information corresponding to an operation, which is performed by a user for resolving an error, for each type of the error, and
an error processing unit that, in a case where occurrence of the error is detected, displays first operation information as at least one piece of operation information with a highest priority among the plurality of pieces of operation information corresponding to the type of the error that has occurred, and in a case where a number of times of the operation corresponding to the first operation information, which is performed by the user, has reached a predetermined number within a predetermined period after the first operation information is displayed, displays server-side operation information corresponding to information on the type of the error that has occurred and information on the number of times of the operation, which is received from the server.

17. The ultrasound system according to claim 16,
wherein the error processing unit is configured as a program for causing a computer to function as the error processing unit, and in a case where the number of times of the operation has reached the predetermined number within the predetermined period, displays server-side operation information corresponding to information on the type of the error that has occurred, information on the number of times of the operation, and information on a version of the program, which is received from the server.

18. An ultrasound system comprising:
an ultrasound probe; and
a handheld information terminal connected to the ultrasound probe in a wired or wireless manner,
wherein the information terminal includes
an operation information storage unit that stores a plurality of pieces of operation information corresponding to an operation, which is performed by a user for resolving an error, for each type of the error, and
an error processing unit that, in a case where occurrence of the error is detected, displays first operation information as at least one piece of operation information with a highest priority among the plurality of pieces of operation information corresponding to the type of the error that has occurred, and in a case where a number of times of the operation corresponding to the first operation information, which is performed by the user, has reached a predetermined number within a predetermined period after the first operation information is displayed, reads second operation information as at least one piece of operation information with the highest priority next to the first operation information, by sound.

19. An ultrasound system comprising:
an ultrasound probe; and
a handheld information terminal connected to the ultrasound probe in a wired or wireless manner,
wherein the information terminal includes
an operation information storage unit that stores a plurality of pieces of operation information corresponding to an operation, which is performed by a user for resolving an error, for each type of the error, and
an error processing unit that, in a case where occurrence of the error is detected, displays first operation information as at least one piece of operation information with a highest priority among the plurality of pieces of operation information corresponding to the type of the error that has occurred, and in a case where a number of times of the operation corresponding to the first operation information, which is performed by the user, has reached a predetermined number within a predetermined period after the first operation information is displayed, displays reference destination information representing a reference destination of related information that relates to the error.

20. A control method of an ultrasound system including an ultrasound probe, and a handheld information terminal connected to the ultrasound probe in a wired or wireless manner, the control method comprising:
storing a plurality of pieces of operation information corresponding to an operation, which is performed by a user for resolving an error, for each type of the error, by an operation information storage unit of the information terminal;
displaying, in a case where occurrence of the error is detected, first operation information as at least one piece of operation information with a highest priority among the plurality of pieces of operation information corresponding to the type of the error that has occurred, by an error processing unit of the information terminal; and
displaying, in a case where a number of times of the operation corresponding to the first operation information, which is performed by the user, has reached a predetermined number within a predetermined period after the first operation information is displayed, second operation information as at least one piece of operation information with the highest priority next to the first operation information, by the error processing unit.

* * * * *